United States Patent [19]

Rameswaran et al.

[11] Patent Number: 5,081,267

[45] Date of Patent: Jan. 14, 1992

[54] EPOXIDATION PROCESS

[75] Inventors: M. Rameswaran; Robert N. Cochran, both of West Chester, Pa.

[73] Assignee: Arco Chemical Technology, Inc., Wilmington, Del.

[21] Appl. No.: 580,426

[22] Filed: Sep. 13, 1990

Related U.S. Application Data

[63] Continuation-in-part of Ser. No. 417,608, Oct. 5, 1989, abandoned.

[51] Int. Cl.⁵ .......................................... C07D 301/19
[52] U.S. Cl. .................................................. 549/529
[58] Field of Search ........................................ 549/529

[56] References Cited

U.S. PATENT DOCUMENTS

| | | | |
|---|---|---|---|
| 3,829,392 | 8/1974 | Wulff | 549/529 |
| 3,923,843 | 12/1975 | Wulff | 549/529 |
| 3,980,586 | 9/1976 | Mitchell | 502/64 |
| 4,157,346 | 6/1979 | Lines et al. | 549/529 |
| 4,197,161 | 4/1980 | Friedrich et al. | 502/41 |
| 4,833,260 | 5/1989 | Neri et al. | 549/531 |

Primary Examiner—C. Warren Ivy
Assistant Examiner—Ba K. Trinh
Attorney, Agent, or Firm—William C. Long

[57] ABSTRACT

The present invention relates to the epoxidation of olefinic compounds by reaction with an organic hydroperoxide in the presence of a solid, heterogeneous catalyst comprised of molybdenum oxide finely dispersed in silica or of both molybdenum oxide and titanium oxide finely dispersed in silica.

8 Claims, No Drawings

EPOXIDATION PROCESS

RELATED APPLICATION

BACKGROUND OF THE INVENTION

This application is a continuation-in-part of copending application 07/417,608 filed Oct. 5, 1989, now abandoned.

1. Field of the Invention

The present invention relates to the epoxidation of olefinically unsaturated compounds and to the preparation of stable heterogeneous catalysts useful in such epoxidations. In particular, the invention relates to preparation of amorphous or crystalline oxide mixtures of silica with molybdenum oxide or with both molybdenum oxide and titanium oxide and to the use of these materials in the epoxidation of olefinically unsaturated compounds.

2. Description of the Prior Art

Processes are known and practiced commercially for the epoxidation of olefins by catalytic reaction of the olefins with an organic hydroperoxide. U.S. Pat. Nos. 3,350,422 and 3,351,635 describe, among other things, the use of compounds of Mo, V, W, Ti and the like as catalysts for the reaction.

Efforts have been made by prior workers to develop heterogeneous catalyst systems useful in such epoxidations which are essentially insoluble in the reaction mixture. U.S. Pat. No. 3,634,464 describes supporting Mo on a support such as silica with added bismuth or rare earth in an effort to provide a heterogeneous catalyst system. U.S. Pat. No. 4,021,454 describes titania on silica, the titania said to be in chemical combination with the silica. U.S. Pat. Nos. 3,829,392 and 3,923,843 deal with oxides and hydroxides of titanium, molybdenum, vanadium, zirconium and boron in chemical combination with silica, the further improvement being that the heterogeneous catalysts are treated with a silylation agent to enhance the performance thereof.

Prior workers have described the preparation of titanium-containing silicalite, see U.S. Pat. No. 4,410,501, and the use of these silicates to catalyze the epoxidation of olefinic materials by reaction with hydrogen peroxide; see U.S. Pat. 4,833,260. These materials are not effective with organic hydroperoxide.

Siliceous crystalline compositions further comprising one or more metals are prepared by admixing a basic silica salt and a dissolved metal salt in the presence of a quaternary ammonium ion and subsequently heating under pressure. Tungsten and molybdenum are included among the metals disclosed. See U.S. Pat. No. 4,828,813.

Despite the efforts of prior workers, there remains considerable room for improvement in the preparation of heterogeneous catalysts and the use thereof in epoxidations. For example, prior efforts to epoxidize olefins with hydroperoxides using insoluble tungsten and molybdenum catalysts have not proved successful since the tungsten and molybdenum has tended to leach from the solid composition.

BRIEF SUMMARY OF THE INVENTION

In accordance with the present invention, olefinically unsaturated compounds are epoxidized with organic hydroperoxides using mixed oxide catalysts of silica together with an oxide of Mo or with oxides of both Mo and Ti characterized in that the oxides of Mo or Mo and Ti are evenly distributed throughout the entire catalyst structure. In particular preferred practice, the catalysts which are used are prepared by procedures involving the hydrolysis of silica alkoxides and compounds of molybdenum or compounds of molybdenum and titanium and the precipitation of stable, well dispersed mixed metal oxides.

DETAILED DESCRIPTION OF THE INVENTION

In preferred practice of the invention, a silica alkoxide such as tetraethoxy silane is hydrolyzed in the presence of a compound of Mo optionally also with a compound of Ti in order to produce a precipitate of the well dispersed mixed metal oxides. For example, an aqueous solution of ammonium dimolybdate or a solution of molybdenum carbonyl in tetrahydrofuran and water is mixed with tetraalkoxy silane such as tetraethoxy silane and the resulting mixture heated to appropriate hydrolysis temperature. Upon hydrolysis, there is formed a precipitate of the mixed oxides characterized in that the molybdenum oxide is finely and uniformly dispersed in the silicon dioxide.

The resulting amorphous oxide mixture can be recovered and used in the epoxidation of olefins. Alternatively, the oxide mixture can be subjected to a hydrothermal recrystallization treatment, e.g. 160° C. at autogenous pressure for several days to form zeolitic crystalline materials which catalyze the epoxidation.

Other molybdenum compounds useful in the preparation of the mixed oxide catalysts include molybdenum chloride, bis cyclopentadienyl bimolybdenum pentacarbonyl, and the like.

In an additional practice of the invention, an aqueous solution of ammonium dimolybdate and titanium alkoxide, eg. titanum butoxide, is mixed with tetraalkoxy silane, eg. tetraethoxy silane, and the resulting mixture heated to appropriate hydrolysis temperature. Upon hydrolysis, there is formed a precipitate of the mixed oxides characterized in that the molybdenum oxide and titanium oxide are finely and uniformly dispersed in the silicon dioxide.

In this case, the amorphous oxide mixture is recovered and can be used in the epoxidation of olefins. The mixture should not be subjected to a hydrothermal recrystallization before use in epoxidations.

Where the catalyst is a mixture of oxides of molybdenum and titanium finely divided and evenly dispersed in silicon dioxide, performance of the catalyst in the epoxidation of olefinic materials by reaction with organic hydroperoxides is greatly improved by silylation of the catalyst before use. Generally known silylation procedures can be used such as are taught in U.S. Pat. Nos. 3,923,843 and 3,829,392 as well as in published European Publication Number 0 345 856.

Illustrative sylylating agents are, for example, organosilanes, organosilylamines and organosilazanes. Preferred are tetra-substituted silanes with 1-3 hydrocarbyl substituents, such as choro trimethyl silane, dichloro dimethyl silane, chloro bromo dimethyl silane, nitro trimethyl silane, chloro triethyl silane, iodo dimethyl butyl silane and chloro dimethyl phenylsilane. A very useful silylating agent is hexamethyldisilazane.

As to epoxidations using the above catalysts, reference is made to U.S. Pat. No. 3,351,635 for a description of suitable olefins, hydroperoxides and reaction ratios and conditions which can be used.

Olefinically unsaturated materials which are epoxidized in accordance with the invention include substituted and unsubstituted aliphatic and alicyclic olefins which may be hydrocarbons or esters or alcohols or ketones or ethers or the like. Preferred compounds are those having from about 2 to 30 carbon atoms, and preferably at least 3 carbon atoms. Illustrative olefins are ethylene, propylene, normal butylene, isobutylene, the pentenes, the methyl pentenes, the normal hexenes, the octenes, the dodecenes, cyclohexenes, methyl cyclohexene, butadiene, styrene, methyl styrene, vinyl toluene, vinylcyclohexene, the phenyl cyclohexenes, and the like. Olefins having halogen, oxygen, sulfur and the like containing substituents can be used. Such substituted olefins are illustrated by allyl alcohol, methallyl alcohol, cyclohexanol, diallyl ether, methyl methacrylate, methyl oleate, methyl vinyl ketone, allyl chloride and the like. In general, all olefinic materials epoxidized by methods previously employed can be epoxidized in accordance with this process including olefinically unsaturated polymers having up to about several thousand carbon atoms. Illustrative olefins are linseed oil, olive oil, soybean oil, cottonseed oil, tall oil glycerides, castor oil, corn oil, butyl-polyglycol esters of unsaturated fatty acids, liquid or solid polybutadiene, polyisoprene, unsaturated copolymers of ethylene and propylene including terpolymers thereof with cyclopentadiene and the like. Propylene is the preferred olefin.

The reaction of this invention is carried out broadly using an organic hydroperoxide reactant having the formula ROOH wherein R is an organic radical. In preferred practice R is a substituted or unsubstituted alkyl, cycloalkyl, aralkyl, aralkenyl, hydroxyaralkyl, cycloalkenyl, hydroxycycloalkyl and the like radical having about 3 to 20 carbon atoms. R may be a heterocyclic radical.

Illustrative and preferred hydroperoxides are cumene hydroperoxide, ethylbenzene hydroperoxide, tertiary butyl hydroperoxide, cyclohexanone peroxide, tetralin hydroperoxide, methyl ethyl ketone peroxide, methylcyclohexene hydroperoxide and the like as well as the hydroperoxides of toluene, p-ethyl toluene, isobutylbenzene, diisopropyl benzene, p-isopropyl toluene, o-xylene, m-xylene, p-xylene, phenyl cyclohexane, etc. A useful organic hydroperoxide compound for use in this invention is the peroxide product which is formed by the liquid phase molecular oxygen oxidation of cyclohexanol.

The reaction conditions which are employed in the epoxidations of this invention can vary quite broadly.

Temperatures which can be employed in the present invention can vary quite widely depending upon the reactivity and other characteristics of the particular system. Temperatures broadly in the range of about $-20°$ to $200°$ C., desirably $0°$ to $150°$ C., and preferably $50°-20°$ C. can be employed. The reaction is carried out at pressure conditions sufficient to maintain a liquid phase. Although sub-atmospheric pressures can be employed, pressures usually in the range of about atmospheric to about 1,000 p.s.i.g. are most desirable.

In the oxidation of the olefinic substrate, the ratio of substrate to organic peroxy compounds can vary over a wide range. Generally, mol ratios of olefinic groups in the substrates to hydroperoxide broadly in the range of 0.5:1 to 100:1, desirably 1:1 to 20:1 and preferably 2:1 to 10:1 are employed.

Generally, in the preparation of the catalysts, up to about 50% by weight based on the entire catalyst of $MoO_3$ is incorporated in the catalyst formulation. Preferred amounts are 0.1 to 10% $MoO_3$.

Where titanium oxide is also incorporated in the catalyst, up to about 20% by weight based on the entire catalyst of $TiO_2$ is incorporated in the catalyst formulation. Preferred amounts are 0.1 to 10% $TiO_2$ by weight of the entire catalyst.

During hydrolysis, it is advantageous to adjust the pH of the hydrolysis mixture as by the addition of acid or base in order to achieve the desired product properties.

The solid heterogeneous catalyst is suitably pretreated or conditioned for the removal of soluble molybdenum values. This can be carried out by contacting the solid catalyst with polar organic materials. It is especially advantageous to pretreat or condition the solid catalyst to remove soluble molybdenum by contact with the hydroperoxide containing epoxidation reactant mixture until the level of soluble molybdenum in the liquid stabilizes at less than about 5 ppm, preferably less than about 1 ppm, thus producing the insoluble catalyst for use in the invention.

The invention can best be illustrated by reference to the following examples.

EXAMPLE 1

A solution of 0.14 grams Mo $(CO)_6$ in 50 ml. tetrahydrofuran (THF) was prepared. To this solution there were slowly added 40 ml. of tetraethoxy silane and 50 ml. of deionized water. The resulting mixture was gradually heated to a temperature of $90°$ C.

After three hours, substantial mixed oxide crystallization had occurred; the mixture was cooled to room temperature, and the mixed oxide precipitate was recovered by filtration and washed with THF and water. The mixed oxide precipitate of molybdenum oxide finely and uniformly dispersed in silicon oxide was dried at $200°$ C. for two hours and represents a catalyst useful in accordance with the invention. The catalyst contained 0.25% Mo calculated as the metal and had a surface area of about 350 m$^2$/gram.

About 0.5 grams of the mixed oxide catalyst was charged to a stirred reactor flask together with 25 grams of octene-1 and 10 grams of ethyl benzene oxidate which consisted by weight of 34% ethyl benzene hydroperoxide, 57.9% ethyl benzene, 2.1% methyl benzyl alcohol and 4.2% acetophenone along with small amounts of other materials. About 1.49 grams of cyclohexyl benzene was also added to the reactor flask to provide an internal analytical standard.

The mixture was heated to $110°$ C. under an argon atmosphere and small samples of reaction liquid were taken and analyzed after 2 hours and after 4 hours time.

Analysis after 2 hours showed 92% ethyl benzene hydroperoxide conversion with selectivity to octene oxide of 55% based on hydroperoxide converted, and after 4 hours 100% hydroperoxide conversion with 53% selectivity to octene oxide based on hydroperoxide. Analysis of the liquid showed 13 ppm soluble molybdenum contained therein.

After this initial conditioning run, a series of epoxidations using the same catalyst sample were carried out. In each case, the reaction liquid was drained from the catalyst and a fresh liquid charge having the same composition described above for the conditioning run was added to the reactor flask. After 7 runs, including the conditioning Run 1, the catalyst was calcined in air at $350°$ C. for 4 hours and recharged to the reactor flask with the same mixture used in Runs 1–7 and reacted at 110° C. After handling losses during calcination, only about 0.35 grams of catalyst remained for testing in Run 8. The following table shows the results obtained:

TABLE 1

| Run | AFTER 2 HOURS | | AFTER 4 HOURS | | SOLUBLE Mo IN EPOXIDATE (PPM) AFTER 4 HOURS |
|---|---|---|---|---|---|
| | % EBHP Conv | % OO*/EBHP** | % EBHP Conv | % OO*/EBHP** | |
| | Conditioning | | | | |
| Run 1 | 92 | 55 | 100 | 53 | 13 |
| Run 2 | 73 | 61 | 84 | 49 | 0.43 |
| Run 3 | 54 | 59 | 71 | 40 | 0.43 |
| Run 4 | 29 | 53 | 56 | 29 | 0.27 |
| Run 5 | 20 | 44 | 44 | 21 | 0.18 |
| Run 6 (115° C.)*** | 27 | 44 | 53 | 23 | 0.3 |
| Run 7 (125° C.)*** | 48 | 37 | 71 | 24 | 0.14 |
| Run 8 | 63 | 58 | 79 | 43 | 0.7 |

*1,2 octene oxide
**ethyl benzene hydroperoxide
***reaction temperature

The results given above show that the catalyst was substantially insoluble in the epoxidation mixture after the conditioning run. Good conversions and selectivities were achieved with the catalyst deactivating with continued use, probably as a result of the deposition of heavy materials on the surface. Calcination essentially restored catalyst activity to nearly the level of that after the conditioning run. The data also show for each run a decline with time of the octene oxide content, probably due to conversion of octene oxide to some condensation derivative.

EXAMPLE 2

About 1.0 grams of ammonium molybdate tetrahydrate was dissolved in 20 grams of deionized water, and to this solution was added 20 grams of isopropyl alcohol and 20 grams of tetrapropyl ammonium hydroxide. About 45.5 grams of tetraethoxy silane were then slowly added to this solution.

A second solution of 2.24 grams of titanium butoxide in 20 grams of isopropyl alcohol was prepared, and this solution was added drop-wise to the first solution with constant stirring. During this addition, temperature was about 27° C., the pH dropped to about 10.2 and a cloudy precipitate was formed. The resulting mixture was heated to 50°–60° C. for one hour, and 100 ml. of deionized water was added. The resulting mixture was stirred and then evaporated by means of a Rotavap, and a solid powder was recovered. This powder was calcined at 400° C. for two hours.

The resulting dry powder contained 0.19 wt. % molybdenum and 2.3 wt. % titanium, each calculated as the metal.

Ten grams of the powder were charged to a flask containing 50 ml. of ethylbenzene. The flask was blanketed with argon, and 4 ml. of trimethyl chloro silane was added. The resulting mixture was agitated at about 150° C. for 4 hours and then cooled to room temperature. The resulting solids were washed thoroughly with ethylbenzene and filtered to recover the solid epoxidation catalyst The solids were dried at 140°–150° C. in a vacuum oven for four hours About 2.0 grams of the mixed oxide catalyst was charged to a stirred reactor flask together with 25 grams of octene-1 and 10 grams of ethyl benzene oxidate which consisted by weight of 34% ethyl benzene hydroperoxide, 57.9% ethyl benzene, 2.1% methyl benzyl alcohol and 4.2% acetophenone along with small amounts of other materials. About 1.40 grams of cyclohexyl benzene was also added to the reactor flask to provide an internal analytical standard.

The mixture was heated to 100° C. under an argon atmosphere and small samples of reaction liquid were taken and analyzed after 2 hours.

Analysis after 2 hours showed 90% ethyl benzene hydroperoxide conversion with selectivity to octene oxide of 63% based on hydroperoxide converted. Analysis of the liquid showed about 4 ppm soluble molybdenum contained therein and less than 1 ppm soluble Ti.

After this initial conditioning run, a series of epoxidations using the same catalyst sample were carried out. In each case, the reaction liquid was drained from the catalyst and a fresh liquid charge having the same composition described above for the conditioning run was added to the reactor flask. The following table shows the results obtained:

TABLE 2

| Run | AFTER 2 HOURS | | SOLUBLE Mo or Ti in EPOXIDATE (PPM) AFTER 2 HOURS | |
|---|---|---|---|---|
| | % EBHP Conv | % OO*/EBHP** | Ti | Mo |
| | Conditioning | | | |
| Run 1 | 90 | 63 | <1 | 4 |
| Run 2 | 71 | 74 | 1 | 2 |
| Run 3 | 70 | 77 | 4 | <2 |
| Run 4 | | | 2 | <2 |
| Run 5 | 68 | 72 | 3 | <2 |

*1,2 octene oxide
**ethyl benzene hydroperoxide

From these results it can be seen that excellent conversions and selectivities were obtained. The catalyst was substantially insoluble exhibited excellent stability.

What is claimed is:

1. The method of epoxidizing an olefinically unsaturated compound which comprises reacting said compound with an organic hydroperoxide at reaction conditions and in the presence of a solid, insoluble catalyst which consists essentially of a mixed oxide of molybdenum or of molybdenum and titanium finely and uniformly dispersed in silicon oxide, said catalyst being prepared by co-hydrolysis of a molybdenum compound or of a molybdenum and titanium compound and a tetraalkoxy silane, the molybdenum in said catalyst being soluble in the epoxidation reaction mixture to the extent of less than 5 ppm.

2. The method of claim 1 wherein said catalyst is prepared by co-hydrolysis of molybdenum hexacarbonyl and a tetraalkoxy silane.

3. The method of claim 1 wherein said catalyst contains up to 50% by weight of molybdenum oxide.

4. The method of claim 1 wherein said catalyst contains 0.1 to 10% by weight molybdenum oxide.

5. The method of claim 1 wherein said olefinically unsaturated compound is propylene.

6. The method of claim 1 wherein said catalyst is prepared by co-hydrolysis of a molybdenum compound, a titanium compound and a tetra alkoxy silane.

7. The method of claim 6 wherein said titanium compound is a titanium alkoxide.

8. The method of claim 6 wherein the said catalyst is silylated before use in the epoxidation.

* * * * *